United States Patent
Singhal et al.

(10) Patent No.: US 8,233,728 B2
(45) Date of Patent: Jul. 31, 2012

(54) EMBEDDED IMAGE QUALITY STAMPS

(75) Inventors: Dave M. Singhal, San Jose, CA (US); Wen-hsiung Chen, Sunnyvale, CA (US); Dihong Tian, San Jose, CA (US)

(73) Assignee: Cisco Technology, Inc., San Jose, CA (US)

( * ) Notice: Subject to any disclaimer, the term of this patent is extended or adjusted under 35 U.S.C. 154(b) by 936 days.

(21) Appl. No.: 12/266,780

(22) Filed: Nov. 7, 2008

(65) Prior Publication Data

US 2010/0119164 A1 May 13, 2010

(51) Int. Cl.
*G06K 9/36* (2006.01)
(52) U.S. Cl. ......... 382/232; 382/233; 382/240; 382/248
(58) Field of Classification Search .................. 382/240, 382/248, 232, 233, 239, 251; 399/366; 347/171; 235/494
See application file for complete search history.

(56) References Cited

U.S. PATENT DOCUMENTS

| 7,044,395 B1 * | 5/2006 | Davis et al. ................... 235/494 |
| 7,113,615 B2 * | 9/2006 | Rhoads et al. ................ 382/100 |
| 7,693,297 B2 * | 4/2010 | Zhang et al. .................. 382/100 |

OTHER PUBLICATIONS

Krishnan, K. et al., "Efficient Transmission of Compressed Data for Remote Volume Visualization," IEEE Transactions on Medical Imaging, vol. 25, No. 9, Sep. 2006, pp. 1189-1199.
Strom, J. et al., Medical Image Compression with Lossless Regions of Interest, Aug. 1, 1996, pp. 1-50.
Menegaz, G. et al., Lossy to Lossless Object-based Coding of 3D MRI Data.

* cited by examiner

*Primary Examiner* — Anh Hong Do
(74) *Attorney, Agent, or Firm* — Edell, Shapiro & Finnan, LLC

(57) ABSTRACT

In an image generation and rendering system, a quality stamp indicative of image fidelity is embedded in image data units resulting from image data compression/encoding. At decoding, the image quality stamp is captured and when the decoded image is rendered, a fidelity indicator is displayed along with the image.

24 Claims, 4 Drawing Sheets

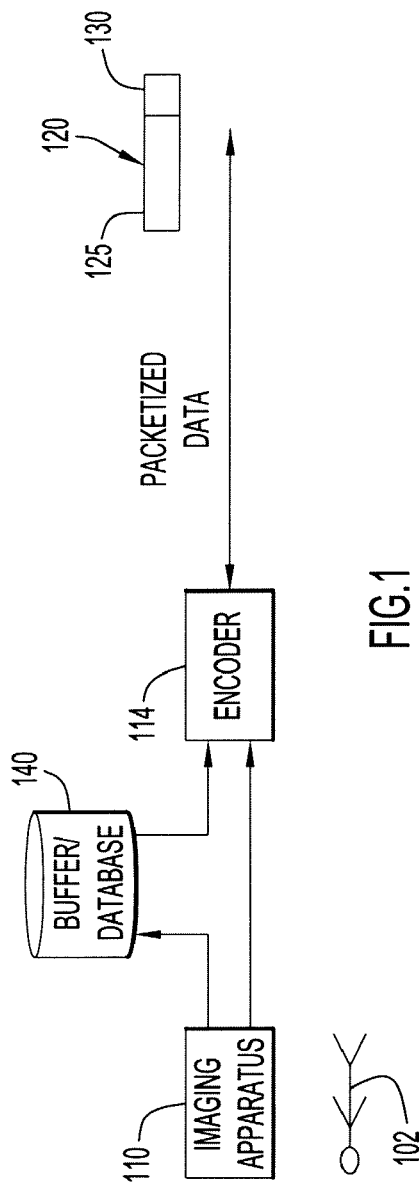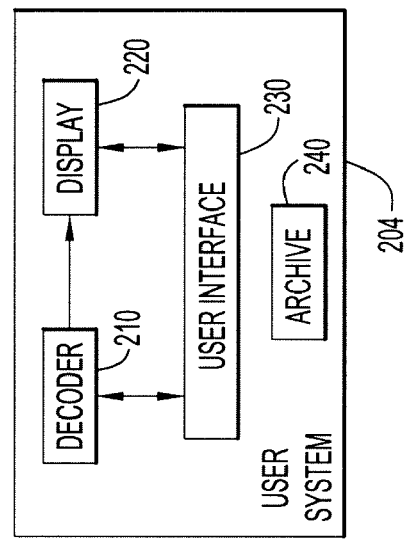

EMBEDDED IMAGE QUALITY STAMPS

TECHNICAL FIELD

Embodiments of the present invention are related to imaging. More particularly, embodiments of the present invention are related to providing or displaying quality level(s) or fidelity information of a given displayed image, where the information is embedded in data units (e.g., packets) during encoding, and made available for display, etc., upon decoding.

BACKGROUND

There is an ever-increasing need for real-time communication and rendering of volumetric images, especially medical images (e.g., computed tomography (CT), magnetic resonance imaging (MRI), etc.) due to rapidly growing demands of, for example, telemedicine, remote collaboration, and distributed networks. Because of the large data volume associated with such images, high compression is often relied upon not only when storing the image, but also when transmitting the same over a network from one point to another. Such data compression (known as "lossy" compression), however, is disadvantageous in that a loss of an image's original fidelity often results. Yet, due to the seriousness of medical diagnostics and procedures, "lossless" reconstruction of an image is, on many occasions, imperative as small image details can influence the detection of pathology and alter a given diagnosis.

One approach to address these competing requirements (lossy vs. lossless compression), is to compress medical images in a scalable and/or object-based fashion, allowing a volumetric image to be rendered, in a first instance, relatively quickly with a lossy reconstruction and then, either automatically or upon command, to be rendered with increased refinement to a point where reconstruction is considered lossless. By limiting or prioritizing the refinement to selected or more important regions, transmission efficiency can be further achieved. Several research efforts in the literature address compression and transmission technologies that support fast visualization and subsequent/selective quality refinement.

BRIEF DESCRIPTION OF THE DRAWINGS

FIGS. 1 and 2 depict the generation and receipt of packetized data in accordance with an embodiment of the present invention;

DESCRIPTION OF EXAMPLE EMBODIMENTS

Overview

Figure 3:
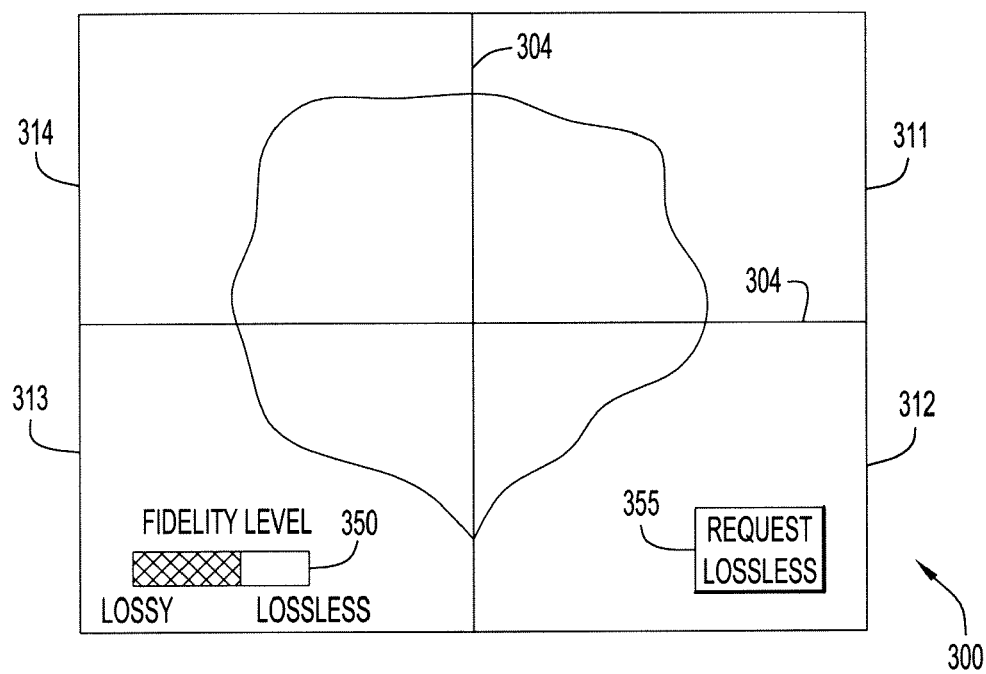
FIGS. 3-6 depict example displays of regions of interest in accordance with embodiments of the present invention.

Embodiments of the present invention provide methods, systems, and logic embedded in a medium for accessing image data representative of an image, compressing, including encoding, the image data for transmission to a user, wherein compressing results in a plurality of compressed image data units, and embedding in each of the compressed image data units a quality stamp indicative of a fidelity level of a corresponding object or region in the image that is to be presented on a display, and decoding such compressed and stamped image data units.

Doctors and technicians are becoming increasingly reliant on three dimensional (3-D) imaging including, for example, MRI, CT, and ultrasound, among others. These imaging technologies generate a significant amount of data, much of which may not actually be of diagnostic value. Nevertheless, all of the data is often stored in a database and provided to one or more image rendering clients (remote or local) upon request. The clients are typically lower cost, less sophisticated computing/rendering devices without the ability to easily store the entirety of a given data set associated with an entire 3-D medical image.

Image data is often stored "slice" by "slice," but the doctor or technician (user) may not need to have a full "lossless" version of each and every slice, or even selected portions of a given slice. Accordingly, interactive techniques have been developed in the prior art to enable the user to request progressive refinement of a given volume of interest (VOI) or region of interest (ROI).

FIGS. 1 and 2 depict the generation and receipt of packetized data in accordance with an embodiment of the present invention. Specifically, an imaging apparatus 110, such as a CT scanning machine, generates an image of a portion of the body of a patient 102. The resulting digital data is thereafter stored in a buffer or database 140, which may be part of imaging apparatus 110 or which may be a stand alone device. Also, although shown as a single device, database 140 may actually comprise a plurality of hardware and software devices distributed in a network.

Although not shown, user system 204 may make a request that a specific image stored in database 140 be displayed on display 220. Such a request may be made via a user interface 230, which may comprise a mouse, keyboard, trackball, among others, as is well-known in the art. Upon receipt of such a request, database 140 outputs a bit stream 112 that is supplied to an encoder 114. Encoder 114 may operate in accordance with any well-known protocol including MPEG, H.264, wavelet, run-length encoding, etc. Packetized data 120 (modified in accordance with embodiments of the present invention as will be explained later herein) is then transmitted over a network, for example, to user system 204. Each packet 120 typically includes a payload portion 125 and a header portion 130. Those skilled in the art will appreciate that packetized data 120 may be further wrapped or packetized or processed in accordance with still other protocols for transmission to a remote location. That is, packetized data 120 may be further encoded in accordance with, e.g., transmission control protocol/internet protocol (TCP/IP), or any other protocol employed to transmit a bit stream from one network device to another.

Ultimately, packetized data 120 is supplied to decoder 210 that is operable to decode packetized data 120 and to provide original image data that is then rendered on display 220. As shown, user interface 230, is in communication, via well-known operating system techniques, with decoder 210 (as necessary) and display 220.

As noted, a user, via user interface 230, may request to view a particular image. In accordance with well-known techniques, that image may, in the first instance, be supplied in a lossy fashion, and only when the user requests, explicitly or implicitly, a further refined version of the image or of a particular region of interest (ROI) will that portion of the image be delivered from encoder 114 in a manner approaching lossless manner, or in a fully lossless manner.

Significantly, existing technologies or medical imaging systems do not provide a methodology or apparatus to indicate to a user the quality level of the image that he/she perceives on display 220. As a result, even though the user may likely be seeing a high-quality or lossless image, he/she is not guaranteed to be making diagnoses based on an image without any artifact in the ROI, which can harm the reliability of his/her decision and, in case of misdiagnoses, cause legal and regulatory disputes.

FIGS. 3-6 depict example displays in accordance with embodiments of the present invention. FIG. 3 shows a displayed view 300 of an image 302 including a cross-hair target 304 that is centered on the center of the view 300 and that creates four ROIs 311, 312, 313, and 314. A fidelity level indicator 350 at the bottom left hand portion of the view 300 indicates how lossy the current view is. In this case, fidelity level indicator 350 is a bar graph that mostly fills the small rectangular window and that, accordingly, indicates that the image 302 that is being displayed is somewhat lossy. That is, the fidelity indicator 350 indicates, in this case, that the packetized data provided by the encoder 114 was not encoded in a lossless fashion. Consequently, the image that is being displayed could be provided in higher resolution.

In one embodiment, display 220 also provides a "button" 355 (selectable by a pointing device in a known manner) that enables the user to request a lossless version of the image currently being displayed. Upon such a request, the view 300 would be rendered with data encoded and then decoded in a lossless manner. Fidelity level indicator 350 would then show a fully filled rectangular window indicating that the best resolution of the image being displayed has been provided to the client side/user system 204.

The user may, in accordance with an embodiment of the present invention, point/click/select with e.g., a mouse, keyboard arrow keys, or trackball, etc. (not shown) one of the ROIs 311-314. Upon such selection, the view on display 220 would change to a "zoomed in" version of the portion of the image 302 that was bounded by the selected ROI (such "zoom" features are well-known in the art). When first requesting such a zoomed in version, the encoder 114 might supply only a lossy version of the zoomed in image such that fidelity indicator 350 would indicate a level that is less than lossless.

Figure 4:
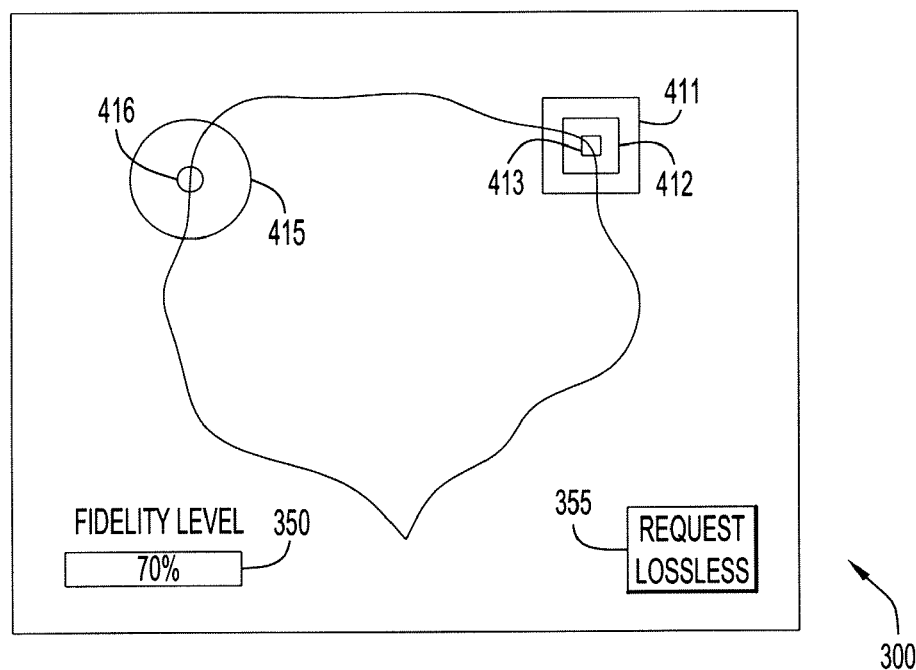
Figure 5:
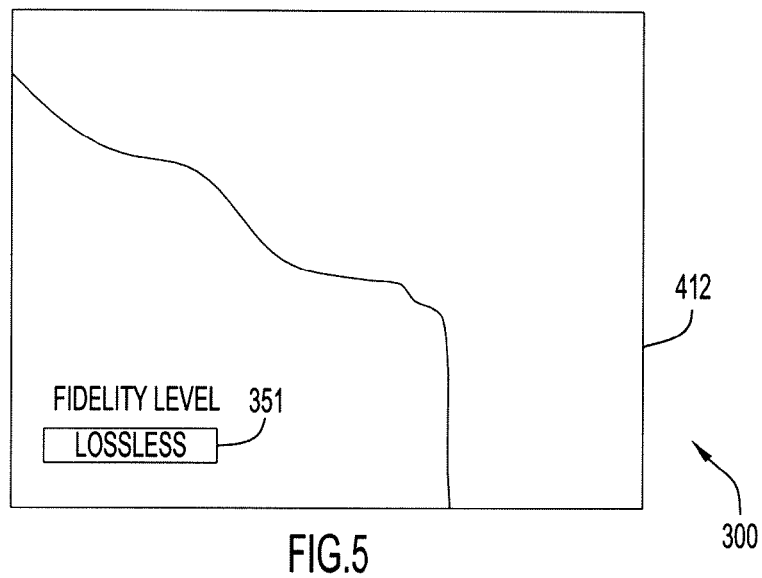
Figure 6:
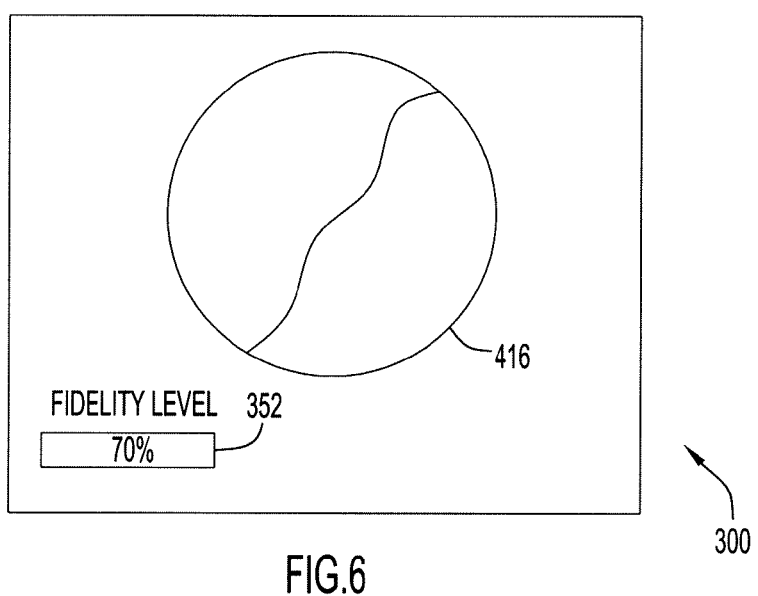

FIG. 4 shows another embodiment for selecting an ROI from an image being displayed. In this case, ROIs can be selected using a custom sizeable rectangular window, several of which (411, 412 or 413) are shown in the figure, enabling the user to select a more custom ROI as compared to the cross-hair overlay embodiment of FIG. 3. The rectangular ROIs 411, 412 and 413 may be selected using, as before, a pointing device such as a mouse, trackball, or any other suitable device.

ROIs 415 and 416 of FIG. 4 are circular or arbitrarily shaped regions rather than rectangular ones, but serve the same overall purpose of enabling a user to select a custom ROI.

FIG. 4 again depicts fidelity level indicator 350. In this case, however, instead of a bar graph type of indicator, the fidelity level is indicated using a numeric value, e.g., "70%" of highest available resolution, or stated alternatively, 70% of lossless resolution. It is noted that there may only be two modes of resolution available in a given system: lossy and lossless. That is, there may not be different levels of "lossyness," but merely a single lossy encoding scheme to supply lossy images, and another encoding scheme to provide lossless images. In that case, and as shown in zoomed-in displays of FIGS. 5 and 6 (which correspond to ROIs 412 and 416 of FIG. 4), fidelity indicator 350 merely toggles between a "lossless" indicator 351 and a "lossy" indicator 352, as shown.

In addition to the described indicia for fidelity level indicator (namely, bar graph, numeric value, or toggled descriptive text, all of which should be considered non-limiting examples), the level of fidelity may also be indicated to a user by changing a background color or boundary frame of the ROI itself. With such an embodiment, the level of fidelity would be immediately clear to a user, without having to distract his/her attention from the image being displayed. As a non-limiting example, traffic light colors may be employed for this purpose according to the following table:

| | |
|---|---|
| Red | Full Lossy |
| Yellow | Partially Lossy (in the event such a mode is available) |
| Green | Lossless |

In addition to the fidelity level indicators described above, the user interface 230 may also provide a means for the user to store/archive the displayed image with its present fidelity status in an unalterable format when making a diagnosis. This can serve as a record for future reference in case of legal or regulatory disputes due to misdiagnoses. A database or archive 240 (shown in FIG. 2) may be used for such purpose.

Figure 7:
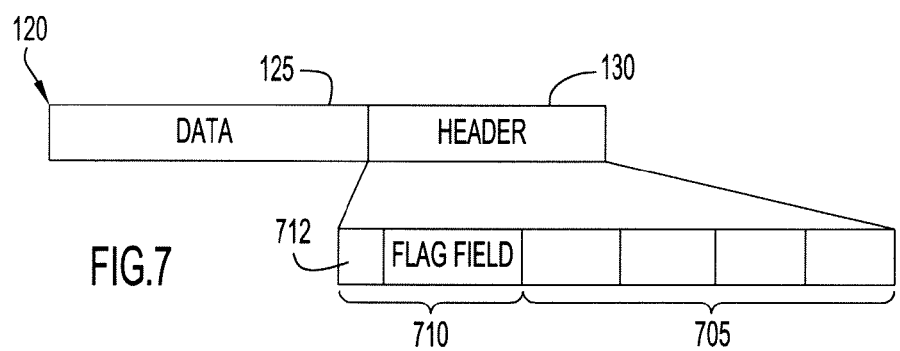
FIG. 7 shows a packet including a header that includes a data quality stamp in accordance with an embodiment of the present invention.

One approach to providing the described fidelity information to a client side user system 204 is to encode a "quality stamp" in the packetized data units 120 that are generated by encoder 114. More specifically, FIG. 7 shows an exploded view of a packetized elementary stream (PES) in accordance with the MPEG standard. As is well-known, each PES packet includes a payload or data portion 125 and a header portion 130. A typical PES packet header 130 includes, among other things, a three byte start code, a one byte stream ID, a two byte length field, a series of indicators including PES_scrambling_control, PES_Priority, a data_alignment_indicator, and copyright information (depicted collectively as 705 in FIG. 7), as well as a flag field 710 that indicates the presence of, e.g., a Presentation Time Stamp (PTS), a Decode Time Stamp (DTS) and cyclic redundancy code (CRC). Thus, there are places in a PES packet header that are either reserved for specific uses, or while reserved for a particular use are not actually relied upon in a given implementation. In an embodiment of the present invention, reserved or unused portions of header portion can be designated for a "quality stamp." Significantly, embodiments of the present invention might need only a single bit or, in most instances, only two bits to represent the quality stamp indicative of the fidelity level of the image information encoded in the given packetized data unit. Thus, for example, a subset 712 of the information in flag field 710, could be used for providing the quality stamp to the decoder 210 of the user system 204. It is also feasible that pre-designated portions of the data portion 130 could be employed to supply the quality stamp, although such an implementation may require more significant modifications to well-known encoder/decoder devices.

In a one bit implementation, the quality stamp would indicate whether the image being supplied is either lossy or lossless, i.e., one of two possibilities, or simply whether the image is above a predetermined quality requirement (e.g., peak signal-to-noise ratio (PSNR)>45 dB). If two (or more) bits are used for the quality stamp, then up to four (or more) different levels of fidelity can be communicated to the user system. In such a case, one of the bit combinations would indicate a lossless encoding scheme, and the remaining possible bit combinations would indicate varying degrees of "lossy-ness"

that would be presented to a user via display 220. The level of lossy-ness indicated is based on the actual encoding process for a given region or image data unit Thus, a focus of an embodiment of the present invention is an image "quality stamp" inserted in every (or a sufficient number of) compressed image data unit that is transmitted to the (remote) client application. The quality stamp indicates the fidelity level of the corresponding object or region in the image after the data unit is correctly decoded. As noted, in one embodiment, such a fidelity level may be a binary flag that indicates whether the corresponding portion of the image has been reconstructed losslessly or not. In a medical image rendering application running on user system 204, the quality stamp is interpreted to a visible format such as a marked boundary or a pseudo color on the corresponding region, or simple text annotation or graphic. In one preferred embodiment, the image rendering application provides options for a user to pull out the quality stamp for a specified region of interest, turn off the quality stamp/fidelity level indicator, or switch between different visualization formats, e.g., text, background color change, both, etc. In another embodiment, a button on the screen or a physical button may allow the user upon depressing the button to toggle on and off the fidelity indicator or to make it flash on and off periodically or cycle through indicator types.

At least one advantage of embodiments of the present invention is the potential for fewer misdiagnoses based on an erroneous reliance on an image that is thought to be the best resolution available. Fewer misdiagnoses may also potentially lead to reduced legal and regulatory consequences. A visualized quality stamp assures medical image observers (users) of the perceptual fidelity of regions of interest, which can prevent misdiagnoses due to imaging artifacts while enabling efficient coding and communication and providing tolerance to lossy reconstruction of the remaining image.

It is noted that the embedded quality stamp(s) of the present invention are distinguishable from "metadata" that may be provided along with data associated with an image data file. Metadata generally refers to data separated from media data that can facilitate the understanding, characteristics, and management usage of the media data. For instance, in the context of a camera, where the data is the photographic image, metadata would typically include the date the photograph was taken and details of the camera settings. Metadata only provides description for a complete content item, i.e., a full stored medical image, or a collection of multiple content items, e.g., a medical image set.

In contrast, the quality stamps described herein are inserted/embedded into the compressed bitstream of the image and are embedded in every (or a sufficient number of) data unit(s). Similar to existing headers as specified by the image coding standards, such information cannot be extracted to metadata but must immediately precede the compression payload. Unlike existing headers, which are generally required for correctly decoding the image data, missing the quality stamp in an optimized embodiment should not disrupt or disturb the decoding process substantially beyond, for instance, increasing the payload size marginally.

It is also noted that there are existing applications that provide both progressive resolution refinement and an indicator showing, e.g., percent completion of a file transfer, sometimes using, for example, a bar graph progress indicator. Those skilled in the art will appreciate, however, that such applications are different from embodiments of the present invention in that a percentage of file transfer indicator merely indicates a transmission progress of a given file or data set, not a quality level of a decoded image nor an indication of which region may have the lossless image data.

Figure 8:
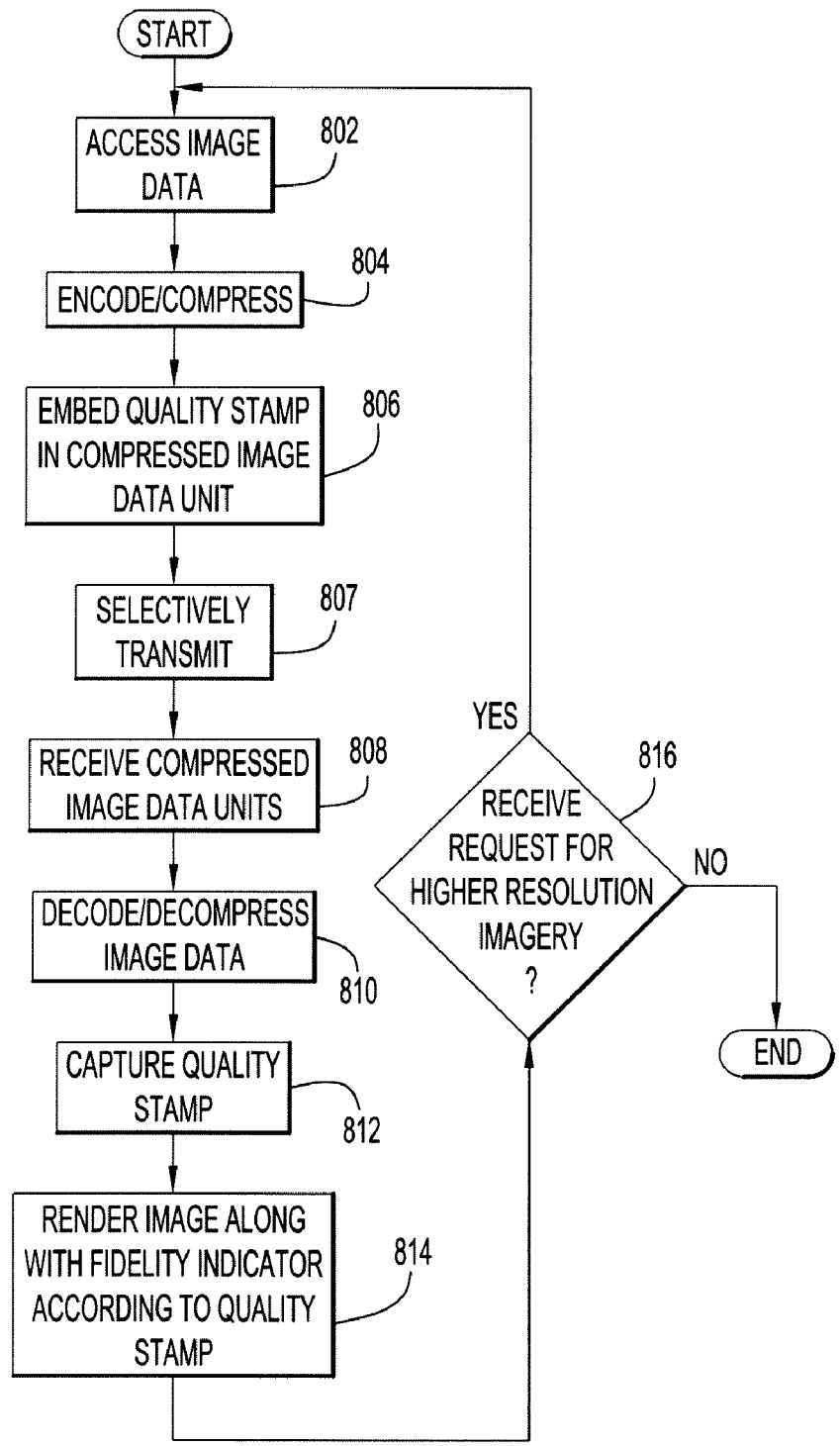
FIG. 8 is a flow chart illustrating an example process for viewing image data with embedded quality stamps in accordance with an embodiment of the present invention.

FIG. 8 is a flow chart illustrating an example process for encoding and viewing image data with embedded quality stamps in accordance with an embodiment of the present invention. As shown, at step 802 image data of the image is accessed. The image data may be stored directly on, for example, a medical imaging device, or in a separately accessible database or buffer. At step 804, the image data is encoded and compressed in accordance with a predetermined protocol such as MPEG. At step 806, which may be part of the encoding step of step 804 but is shown separately for clarity, a quality stamp is embedded in each (or a sufficient number of) compressed data unit (e.g., packet) that results from the encoding step. The quality stamp is an indicator of the level of fidelity at which the image data was encoded. In a simple embodiment, the quality stamp will be indicative of a lossy or lossless encoding methodology. In more sophisticated embodiments, the quality stamp is indicative of one of a plurality of possible levels of fidelity.

The thus encoded image data may then be delivered (or first stored and then delivered) to a user system. In particular, as is indicated by step 807, image data may be selectively transmitted to the user (i.e., not all data of an entire image or portion of an image need necessarily be sent). At the user system, and as further shown in FIG. 8, the compressed image data is received at step 808, and is thereafter decoded/decompressed at step 810 to obtain the originally-encoded image data. At step 812 (which may be incorporated as part of step 810) the embedded quality stamp is captured from each given compressed image data unit.

Thereafter, the image data is rendered on a display for the user. Along with the image, a fidelity indicator, according to the quality stamp, is displayed for the user. The fidelity indicator may be textual, or graphic in nature including boundary color and background color manipulation.

As further shown in FIG. 8, once the image is rendered, a user may have the ability to request a higher resolution version of the entire image, or a particular region of interest. Thus, as shown at step 816, it is determined whether the user has requested higher resolution imagery. Such a request may be made explicitly (e.g., pressing a button) or implicitly (e.g., hovering over a given portion of a displayed image). If so, that request is passed back such that the image data can be again accessed and that image data can be encoded with a higher resolution. In that process, a new quality stamp will be embedded in the resulting individual compressed image data units, which quality stamp, once rendered as the fidelity indicator, will provide an indication to the user of the level of fidelity of the image that is then-being shown.

In another embodiment, the image data is pre-encoded into multiple ROIs, each with multiple quality levels. The compressed image data units are transmitted selectively during a real-time session, upon the aforementioned user request If no request for higher resolution imagery is received, then the process ends.

The steps of FIG. 8 may be implemented in combinations of computer hardware and software, as those skilled in the art will appreciate. Further, logic, embedded in a tangible medium (e.g., memory, hard drive, etc.) may be employed to perform one or more of the functions described herein.

Because only a selected ROI may be encoded with a higher resolution, while leaving other portions of the image encoded with lower resolution, a given image is thus delivered with multiple packets, where some of those packets include a first quality stamp and some include a second quality stamp, where the first and second quality stamps are different and indicate a fidelity level for different parts of the image. The notation on the fidelity indicator 350 may therefore be based on the location of a pointing device.

In sum, embodiments of the present invention provide, among other things, accessing image data representative of an image, encoding the image data for transmission to a user, wherein encoding results in a plurality of compressed image data units, and embedding in each of the compressed image data units a quality stamp indicative of a fidelity level of a corresponding object or region in the image that is to be presented on a display.

Although the apparatus, system, and method are illustrated and described herein as embodied in one or more specific examples, it is nevertheless not intended to be limited to the details shown, since various modifications and structural changes may be made therein without departing from the scope of the apparatus, system, and method and within the scope and range of equivalents of the claims. Accordingly, it is appropriate that the appended claims be construed broadly and in a manner consistent with the scope of the apparatus, system, and method, as set forth in the following.

What is claimed is:

1. A method, comprising:
    accessing image data representative of an image, the image data being stored in a database communicatively coupled to an imaging apparatus with which the image data was generated;
    encoding the image data for transmission to a user, wherein the encoding results in a plurality of compressed image data units; and
    embedding in each of the compressed image data units a quality stamp indicative of a fidelity level of a corresponding object or region in the image that is to be presented on a display.

2. The method of claim 1, further comprising storing the image data in a buffer.

3. The method of claim 1, wherein the encoding comprises encoding the image data in accordance with a predetermined protocol.

4. The method of claim 3, wherein the predetermined protocol is one of MPEG, H.264, wavelet or run-length encoding.

5. The method of claim 1, further comprising embedding the quality stamp in a header portion of at least one of the compressed image data units.

6. The method of claim 1, further comprising displaying indicia, based on the quality stamp, indicative of a fidelity level of the image being presented on the display.

7. The method of claim 6, further comprising rendering a boundary around at least a portion of a region of interest of the image to indicate the level of fidelity.

8. The method of claim 6, further comprising rendering a background color change, based on the quality stamp, indicative of a fidelity level of the image being presented on the display.

9. The method of claim 6, further comprising rendering a textual annotation, based on the quality stamp, indicative of a fidelity level of the image being presented on the display.

10. The method of claim 1, further comprising switching among rendered indicia indicative of a fidelity level of the image being presented on the display.

11. The method of claim 1, further comprising detecting the quality stamp during a decoding process.

12. The method of claim 1, further comprising receiving a request for higher resolution imagery.

13. The method of claim 12, further comprising:
    accessing the image data representative of the image; and
    at least one of:
        re-encoding, at least a portion of the image data at a resolution level higher than a prior resolution level, for transmission to the user, or
        transmitting selectively pre-encoded data units upon user requests.

14. The method of claim 13, further comprising updating a displayed fidelity indicator in accordance with the quality stamp embedded in the compressed data units resulting from the re-encoding.

15. A system, comprising:
    an encoder configured to receive image data and to encode the image data in accordance with a predetermined standard, and further configured to embed in at least selected packets resulting from encoding a quality stamp that is indicative of a level of fidelity with which the image data is encoded.

16. The system of claim 15, further comprising a database in which the image data is stored.

17. The system of claim 16, further comprising an imaging apparatus configured to be in communication with the database that generates the image data.

18. The system of claim 17, wherein the imaging apparatus is a medical imaging apparatus.

19. A system, comprising:
    a decoder and a display, wherein the display is configured to render an image from encoded image data units received and decoded by the decoder, the decoder is further configured to decode a quality stamp embedded in selected encoded image data units, the quality stamp being indicative of a level of fidelity with which the image data was encoded.

20. The system of claim 19, wherein the display is configured to render a fidelity indicator that indicates a level of fidelity in accordance with the quality stamp.

21. The system of claim 19, wherein the individual encoded image data units are individual packets.

22. The system of claim 19, further comprising a user interface that is configured to receive, explicitly or implicitly, a request for a higher resolution or a lossless image.

23. The system of claim 19, further comprising means for storing as an archive a rendered image along with its indicated level of fidelity.

24. Logic encoded in a non-transitory computer-readable medium for execution and when executed operable to:
    access image data representative of an image;
    encode the image data for transmission to a user, wherein encoding results in a plurality of compressed image data units; and
    embed in each of the compressed image data units a quality stamp indicative of a fidelity level of a corresponding object or region in the image that is to be presented on a display.

* * * * *